US012801853B2

(12) United States Patent
Biryukov et al.

(10) Patent No.: US 12,801,853 B2
(45) Date of Patent: Nov. 17, 2026

(54) TRANSACTION BASED NAMED ENTITY RECOGNITION USING PAIR OF TRANSACTION RECORDS TRAINING DATA

(71) Applicant: Ramp Business Corporation, New York, NY (US)

(72) Inventors: Anton Biryukov, Calgary (CA); Yunyu Lin, New York, NY (US)

(73) Assignee: Ramp Business Corporation, New York, NY (US)

( * ) Notice: Subject to any disclaimer, the term of this patent is extended or adjusted under 35 U.S.C. 154(b) by 260 days.

(21) Appl. No.: 18/642,505

(22) Filed: Apr. 22, 2024

(65) Prior Publication Data

US 2025/0328734 A1 Oct. 23, 2025

(51) Int. Cl.

| | |
|---|---|
| ***G06F 40/295*** | (2020.01) |
| ***G06F 16/21*** | (2019.01) |
| ***G06Q 10/063*** | (2023.01) |
| ***G06Q 20/38*** | (2012.01) |
| ***G06Q 20/40*** | (2012.01) |
| ***G06Q 50/26*** | (2024.01) |
| ***G16H 50/20*** | (2018.01) |

(52) U.S. Cl.

CPC ......... *G06F 40/295* (2020.01); *G06Q 20/389* (2013.01); *G06Q 20/401* (2013.01); *G06Q 20/405* (2013.01); *G06F 16/219* (2019.01); *G06Q 10/063* (2013.01); *G06Q 50/26* (2013.01); *G16H 50/20* (2018.01)

(58) Field of Classification Search

CPC .. G06Q 20/389; G06Q 20/401; G06Q 20/405; G06Q 10/063; G06F 16/219

USPC ............................................................ 705/2

See application file for complete search history.

(56) References Cited

U.S. PATENT DOCUMENTS

2022/0318925 A1* 10/2022 Pei ......................... G06N 20/00
2022/0398670 A1 12/2022 Howard et al.
(Continued)

FOREIGN PATENT DOCUMENTS

KR 20140115078 A * 3/2013 ........... G06Q 10/063

OTHER PUBLICATIONS

Patent Cooperation Treaty, International Search Report and Written Opinion, PCT Application No. PCT/US2025/018470, May 22, 2025, 14 pages.

*Primary Examiner* — Farzad Kazeminezhad
(74) *Attorney, Agent, or Firm* — Fenwick & West LLP

(57) ABSTRACT

A server uses a transformer model to identify a named entity associated with a transaction record. The server receives a transaction record including a text string that includes a non-normalized version of a name of a named entity. The server generates a first embedding of the text string using a first transformer model and identifies a set of similar transactions by comparing the first embedding to second embeddings representing the similar transactions. The server inputs the text string of the transaction record and the set of similar transactions into a second transformer model. The server receives an output from the second transformer and determines that the output indicates that the non-normalized version of the name in the transaction record is classifiable to one of the normalized named entities in the list. The server associates the transaction record with the normalized named entity to which the non-normalized named entity is classifiable.

20 Claims, 4 Drawing Sheets

(56) References Cited

U.S. PATENT DOCUMENTS

| | | | |
|---|---|---|---|
| 2022/0405477 A1 | 12/2022 | Lee et al. | |
| 2023/0185796 A1* | 6/2023 | Subramanian | G06F 16/219 705/2 |
| 2023/0214831 A1 | 7/2023 | Lee et al. | |
| 2023/0359648 A1* | 11/2023 | Kalambe | G06F 16/215 |
| 2024/0013211 A1 | 1/2024 | Edwards et al. | |
| 2024/0078466 A1 | 3/2024 | Sharma et al. | |
| 2024/0177818 A1* | 5/2024 | Goravar | G16H 50/20 |

* cited by examiner

TRANSACTION BASED NAMED ENTITY RECOGNITION USING PAIR OF TRANSACTION RECORDS TRAINING DATA

TECHNICAL FIELD

The present disclosure generally relates to named entity recognition, particularly, named entity recognition using a transformer model.

BACKGROUND

A transaction server manages the authentication and approval of transactions between parties. Often, transaction servers are required to identify one or more parties associated with the transaction for these authentication and approval services. Typical transaction servers might rely on a named entity recognition process that identifies named entities in transaction records based on string similarity metrics. For example, a transaction including the string "HEXA" might be identified as a named entity "Hexagon" because of the string similarity between the two strings. However, due to the amount of extraneous or spurious information in transaction strings (e.g., random numbers and random strings that are not related to the name of the named entity) as well as the tendency for named entity names to be abbreviated, misspelled, and generally non-normalized, this method often produces false positives. In cases where the identification of named entities is the difference between authenticating or not authenticating a transaction—and likewise approving or not approving a transaction—it is critical for a transaction server to identify named entities with high accuracy.

SUMMARY

Embodiments are related to named entity recognition processes that use transformer models to identify named entities associated with transaction records. In one embodiment, a computing server applies a transformer model to the text of a transaction record and a set of similar transaction records. The transformer model is trained on pairs of transactions labeled by whether they correspond to the same named entity. The transformer model is trained to classify a non-normalized version of a named entity name in the text string of the transaction record to a normalized named entity name in a list of candidate normalized named entity names. In an inference process, the transformer model identifies which of the similar transactions has the same named entity as the transaction record and identifies the normalized named entity name associated with the identified similar transaction. The transformer model outputs a normalized named entity name to which the non-normalized named entity name may be classified.

In some embodiments, the computing server receives a transaction record. The transaction record includes a text string that includes a non-normalized version of a name of a named entity. The computing server generates a first embedding of the text string using a first transformer model. The computing server identifies a set of similar transactions using the first embedding by comparing the first embedding representing the transaction record to second embeddings representing the similar transactions. The computing server inputs the text string of the transaction record and the set of similar transactions in natural language into a second transformer model to request the second transformer model to determine whether the non-normalized version of the name of the named entity is classifiable to a normalized named entity in a list of candidate normalized named entities. The computing server receives an output from the second transformer model and determines that the output indicates that the non-normalized version of the name in the transaction record is classifiable to one of the normalized named entities in the list. The computing server associates the transaction record with the normalized named entity to which the non-normalized named entity is classifiable.

Figure 1:
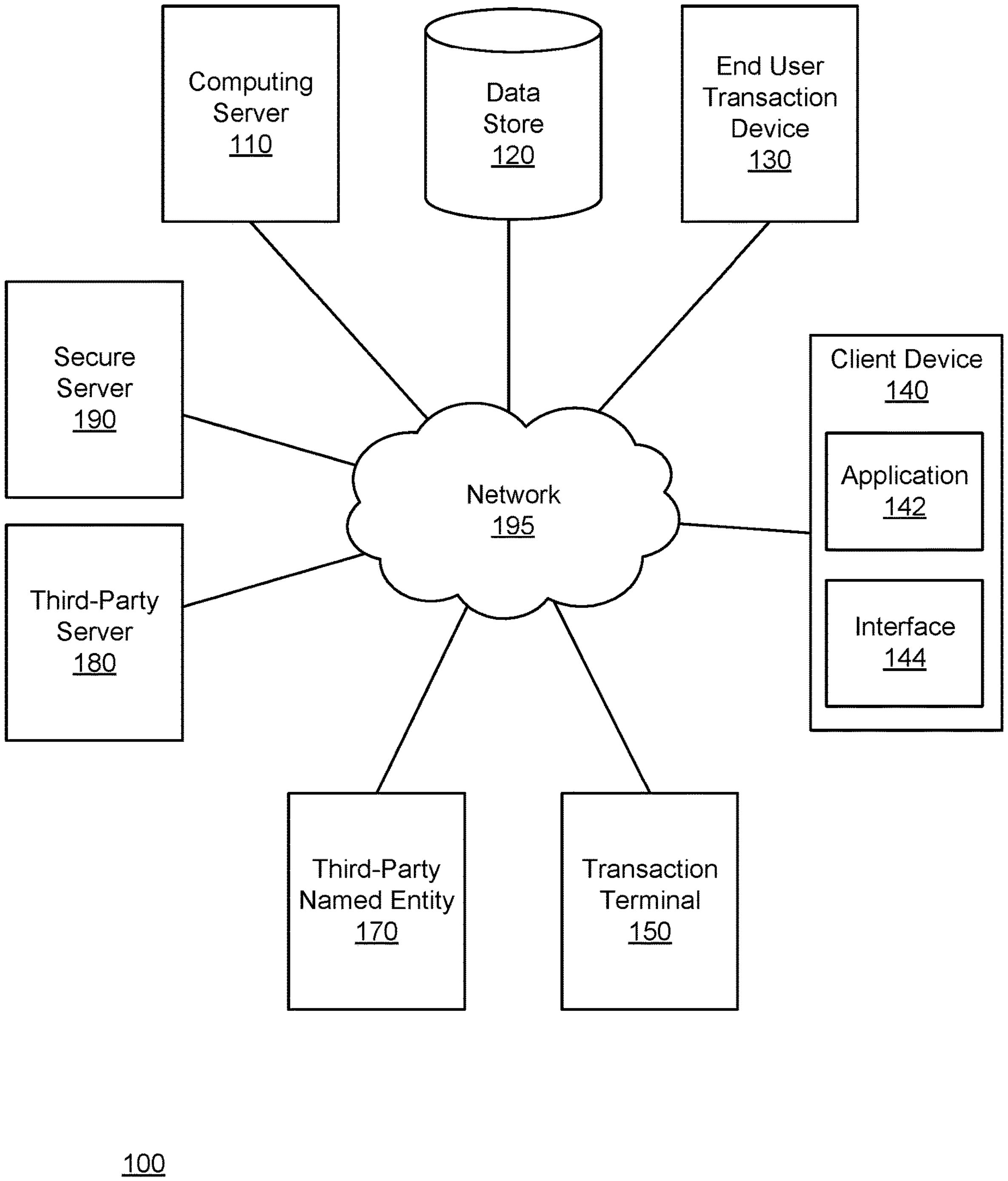
FIG. 1 is a block diagram illustrating an example system environment, in accordance with some embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

System Overview

FIGURE (FIG.) 1 is a block diagram that illustrates an automated record matching system environment 100, in accordance with some embodiments. The system environment 100 includes a computing server 110, a data store 120, an end user transaction device 130, a client device 140, a transaction terminal 150, a third-party named entity 170, a third-party server 180, and a secure server 190. The entities and components in the system environment 100 communicate with each other through a network 195. In various embodiments, the system environment 100 includes fewer or additional components. In some embodiments, the system environment 100 also includes different components. While each of the components in the system environment 100 is described in a singular form, the system environment 100 may include one or more of each of the components. For example, in many situations, the computing server 110 can communicate with multiple end user transaction devices 130 for different end users, who interact with various third-party named entities 170. Different client devices 140 may also access the computing server 110 simultaneously.

The computing server 110 includes one or more computers that perform various tasks related to managing certain transactions on behalf of clients and automatically matching transactions of various clients to documentation records of those transactions that may be generated in other sources. For example, the computing server 110 may create transaction cards (e.g., credit cards) and accounts for an organization client and manages transactions of the cards based on rules set by the client (e.g., pre-authorization and restrictions on certain transactions). Examples of organizations may include commercial businesses, educational institutions, private or government agencies, or any suitable group of one or more individuals that engage in transactions with a named entity (e.g., a merchant) using an account associated with a transaction card. An end user may be a member of an organization client such as an employee of the organization or an individual that uses transaction cards to make purchase from a merchant. In some embodiments, the computing server 110 provides its clients with various payment, spending, and record matching and management services as a form of cloud-based software, such as software as a service (SaaS). Examples of components and functionalities of the computing server 110 are discussed in further detail below with reference to FIG. 2. The computing server 110 may provide a SaaS platform for various clients to manage their accounts and transaction rules related to the accounts.

The data store 120 includes one or more computing devices that include memory or other storage media for storing various files and data of the computing server 110. The data stored in the data store 120 includes accounting information, transaction data, credit card profiles, card rules and restrictions, merchant profiles, merchant identification rules, documentation records, record verification rules, and other related data associated with various clients of the computing server 110. In various embodiments, the data store 120 may take different forms. In some embodiments, the data store 120 is part of the computing server 110. For example, the data store 120 is part of the local storage (e.g., hard drive, memory card, data server room) of the computing server 110. In some embodiments, the data store 120 is a network-based storage server (e.g., a cloud server). The data store 120 may be a third-party storage system such as AMAZON AWS, DROPBOX, RACKSPACE CLOUD FILES, AZURE BLOB STORAGE, GOOGLE CLOUD STORAGE, etc. The data in the data store 120 may be structured in different database formats such as a relational database using the structured query language (SQL) or other data structures such as a non-relational format, a key-value store, a graph structure, a linked list, an object storage, a resource description framework (RDF), etc. In some embodiments, the data store 120 uses various data structures mentioned above.

An end user transaction device 130 is a device that enables the holder of the device 130 to perform a transaction with a party (e.g., a named entity), such as making a payment to a merchant for goods and services based on information and credentials stored at the end user transaction device 130. An end user transaction device 130 may also be referred to as an end user payment device. Examples of end user transaction devices 130 include transaction cards such as credit cards, debit cards, and prepaid cards, other smart cards with chips such as radio frequency identification (RFID) chips, portable electronic devices such as smart phones that enable payment methods such as APPLE PAY or GOOGLE PAY, and wearable electronic devices. The computing server 110 may be the party that issues the end user transaction devices 130 such as credit cards for its organization clients and may impose spending control rules and restrictions on those cards. While credit cards are often used as examples in the discussion of this disclosure, various architectures and processes described herein may also be applied to other types of end user transaction devices 130. In some cases, an end user transaction device 130 may also be a virtual device such as a virtual credit card.

A client device 140 is a computing device that belongs to a client of the computing server 110 or an end user, such as an employee of an organizational client of the computing server 110. A client uses the client device 140 to communicate with the computing server 110 and performs various payment, spending, and record management related tasks such as creating credit cards and associated payment accounts, setting transaction and record verification rules and restrictions on cards, setting pre-authorized or prohibited merchants or merchant categories (e.g., entertainment, travel, education, health, etc.), and matching transactions and records (e.g., verifying a documentation record). The user of the client device 140 may be a manager, an accounting administrator, or a general employee of an organization. While in this disclosure a client is often described as an organization, a client may also be a natural person or a robotic agent. A client may be referred to an organization or its representative such as its employee.

A client device 140 includes one or more applications 142 and interfaces 144 that may display visual elements of the applications 142. In some embodiments, one example of the application may be a web browser application 142 and its corresponding front-end rendering serving as the interface 144. The client device 140 may be any computing device. Examples of such client devices 140 include personal computers (PC), desktop computers, laptop computers, tablets (e.g., iPad), smartphones, wearable electronic devices such as smartwatches, or any other suitable electronic devices.

The application 142 is a software application that operates at the client device 140. In some embodiments, an application 142 is published by the party that operates the computing server 110 to allow clients to communicate with the computing server 110. For example, the application 142 may be part of a SaaS platform of the computing server 110 that allows a client to create transaction cards and accounts and perform various payment, spending, and record management tasks (e.g., confirm documentation records have been verified).

In various embodiments, an application 142 may be of different types. In some embodiments, an application 142 is a web application that runs on JavaScript and other backend algorithms. In the case of a web application, the application 142 cooperates with a web browser to render a front-end interface 144. In another embodiment, an application 142 is a mobile application. For example, the mobile application may run on Swift for iOS and other APPLE operating systems or on Java or another suitable language for ANDROID systems. In yet another embodiment, an application 142 may be a software program that operates on a desktop computer that runs on an operating system such as LINUX, MICROSOFT WINDOWS, MAC OS, or CHROME OS.

An interface 144 is a suitable interface for a client to interact with the computing server 110. The client may communicate to the application 142 and the computing server 110 through the interface 144. The interface 144 may take different forms. In some embodiments, the interface 144 may be a web browser such as CHROME, FIREFOX, SAFARI, INTERNET EXPLORER, EDGE, etc. and the application 142 may be a web application that is run by the web browser. In some embodiments, the interface 144 is part of the application 142. For example, the interface 144 may be the front-end component of a mobile application or a desktop application. In some embodiments, the interface 144 also is a graphical user interface (GUI) which includes graphical elements and user-friendly control elements. In some embodiments, the interface 144 does not include graphical elements but communicates with the data store 120 via other suitable ways such as application program interfaces (APIs), which may include conventional APIs and other related mechanisms such as webhooks.

In some embodiments, the client device 140 and the end user transaction device 130 belong to the same domain. For example, a company client can request the computing server 110 to issue multiple company credit cards for the employees. A domain refers to an environment in which a system operates and/or an environment for a group of units and individuals to use common domain knowledge to organize activities, information and entities related to the domain in a specific way. An example of a domain is an organization, such as a business, an institute, or a subpart thereof and the data within it. A domain can be associated with a specific domain knowledge ontology, which could include representations, naming, definitions of categories, properties, logics, and relationships among various concepts, data, transactions, and entities that are related to the domain. The boundary of a domain may not completely overlap with the boundary of an organization. For example, a domain may be a subsidiary of a company. Various divisions or departments of the organization may have their own definitions, internal procedures, tasks, and entities. In other situations, multiple organizations may share the same domain.

A transaction terminal 150 is an interface that allows an end user transaction device 130 to make electronic fund transfers with a third party such as a third-party named entity. Electronic fund transfer can be credit card payments, automated teller machine (ATM) transfers, direct deposits, debits, online transfers, peer-to-peer transactions such as VENMO, instant-messaging fund transfers such as FACEBOOK PAY and WECHAT PAY, wire transfer, electronic bill payment, automated clearing house (ACH) transfer, cryptocurrency transfer, blockchain transfer, etc. Depending on the type of electronic fund transfers, a transaction terminal 150 may take different forms. For example, if an electronic fund transfer is a credit card payment, the transaction terminal 150 can be a physical device such as a point of sale (POS) terminal (e.g., a card terminal) or can be a website for online orders. An ATM, a bank website, a peer-to-peer mobile application, and an instant messaging application can also be examples of a transaction terminal 150. The third party is a transferor or transferee of the fund transfer. For example, in a card transaction, the third party may be a named entity (e.g., a merchant). In an electronic fund transfer such as a card payment for a merchant, the transaction terminal 150 may generate a transaction data payload that carries information related to the end user transaction device 130, the merchant, and the transaction. The transaction data payload is transmitted to other parties, such as credit card companies or banks, for approval or denial of the transaction.

A third-party named entity 170 may be a third party that conducts transaction with a client of the computing server 110. Third party may be viewed from the perspective of the computing server 110. A named entity may be an identifiable real-world entity. For example, a specific merchant may be a named entity that provides goods or services for purchase by a user using the end user transaction device 130, such as in the situation where an employee uses a virtual credit card issued by the computing server 110 on behalf of the employer to make a purchase with a merchant. Another example of a third-party named entity 170 is a bank which conducts transactions with a company that is the client of the computing server 110. In some embodiments, a third-party named entity 170 may be in control of a transaction terminal 150. For example, a retail chain may be in control of its POS system at a store.

In various embodiments, a third-party named entity 170 may automatically generate a documentation record to document an occurred transaction. The documentation record, which may also simply be referred to as a record, may be generated by the transaction terminal 150 or a server of the named entity. A documentation record serves as a record of a transaction between a named entity and an end user. For example, after a purchase using a POS terminal, the terminal (which broadly may mean the terminal itself or the server of the terminal) may automatically generate a paper or an electronic receipt (e.g., an email receipt) for the customer. A documentation record can include the name of the named entity, a location at which the transaction occurred, a time at which the transaction occurred, an amount which was exchanged during the transaction (e.g., an amount of currency), an itemized list of goods or services purchased, a whole or portion of an identifier of the end user transaction device 130 (e.g., the last four digits of a credit card number), any suitable data describing the transaction, or a combination thereof. The transaction terminal 150 may provide the generated documentation record to the end user transaction device 130, a computing device of the end user (e.g., a laptop computer of the end user), the computing server 110, the secure server 190, or a combination thereof. In some embodiments, the documentation record may be included within the transaction data payload. The documentation record may take various forms, including a paper receipt, a digital image of a paper receipt, an email, a short message service (SMS) text, a Quick Response (QR) code, a physical invoice, an electronic invoice, a statement, or any suitable form for providing data describing a transaction to the end user, the computing server 110, or the secure server 190. The documentation record may be an electronic receipt automatically sent from the third-party named entity 170 in response to the occurrence of a real-time transaction.

The third-party server 180 may include one or more computers that perform various tasks related to receiving automatically generated documentation records from the transaction terminal 150 and transmitting communication payloads to the computing server 110 or the secure server 190. A third-party may operate the third-party server 180. In some embodiments, the third-party that operates the third-party server 180 may be the third-party named entity 170. In some embodiments, the third-party that operates the third-party server 180 may be a third-party unrelated to the third-party named entity 170.

The secure server 190 is a computing server that may have a heightened security standard and an isolated environment for connecting with the third-party server 180 and reviewing data from the third-party server 180 that may include personally identifiable information or other sensitive information. In some embodiments, the secure server 190 may receive data from the third-party server 180 directly or from another party such as a mailbox provider of the organization associated with the third-party server 180. The secure server 190 may establish a connection with a mailbox provider to receive message data such as the email data of the organization. The extent of information received by secure server 190 may depend on an agreement between organization and the secure server 190. For example, in some embodiments, the secure server 190 may receive only certain header fields of the message data. In other embodiments, the secure server 190 may receive the entire headers of the message data. In other embodiments, the secure server 190 may receive the body of the messages such as the content of the emails. In other embodiments, the secure server 190 may also receive reports such as message management reports that may or may not contain some or all of the content of the messages. The secure server 190 may analyze the message data and filter the data before the outputs of the secure server 190 are sent to the computing server 110.

In some embodiments, the secure server 190 may communicate with the third-party server 180 via various suitable ways. In some embodiments, an application programming interface (API) allows the secure server 190 to inspect some of the messages, such as emails, directed to or in transit in the third-party server 180. In some embodiments, the API may provide access to the secure server 190 for all contents of the messages or for only part of the data of the messages. In some embodiments, the secure server 190 may include in-line processing of emails.

In some embodiments, the computing server 110 may automatically match documentation records that are generated by a third-party named entity 170 in transactions between various end users and the third-party named entity 170 to the transactions. An organization client may delegate the computing server 110 to manage and approve real-time transactions that involve the use of end user transaction devices 130 of the organization with various third-party named entities 170 (e.g., various merchants). The computing server 110, upon reviewing and approving a transaction in real time, retains a record of the transaction. On the other hand, the third-party named entity 170 may separately generate a documentation record (e.g., an e-receipt) for the transaction. The third-party named entity 170 may transmit the documentation record to the third-party server 180. In turn, the computing server 110, whether directly or through the secure server 190 first filtering the data, may obtain data from the third-party server 180. The computing server 110 automatically identify the documentation record and match the documentation to the transaction that was approved the computing server 110.

Various servers in this disclosure may take different forms. In some embodiments, a server is a computer that executes code instructions to perform various processes described in this disclosure. In another embodiment, a server is a pool of computing devices that may be located at the same geographical location (e.g., a server room) or be distributed geographically (e.g., clouding computing, distributed computing, or in a virtual server network). In some embodiments, a server includes one or more virtualization instances such as a container, a virtual machine, a virtual private server, a virtual kernel, or another suitable virtualization instance.

The network 195 provides connections to the components of the system environment 100 through one or more subnetworks, which may include any combination of local area and/or wide area networks, using both wired and/or wireless communication systems. In some embodiments, a network 195 uses standard communications technologies and/or protocols. For example, a network 195 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 195 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 195 may be represented using any suitable format, such as hypertext markup language (HTML), extensible markup language (XML), JavaScript object notation (JSON), structured query language (SQL). In some embodiments, some of the communication links of a network 195 may be encrypted using any suitable technique or techniques such as secure sockets layer (SSL), transport layer security (TLS), virtual private networks (VPNs), Internet Protocol security (IPsec), etc. The network 195 also includes links and packet switching networks such as the Internet. In some embodiments, a data store belongs to part of the internal computing system of a server (e.g., the data store 120 may be part of the computing server 110). In such cases, the network 195 may be a local network that enables the server to communicate with the rest of the components.

Example Server Components

Figure 2:
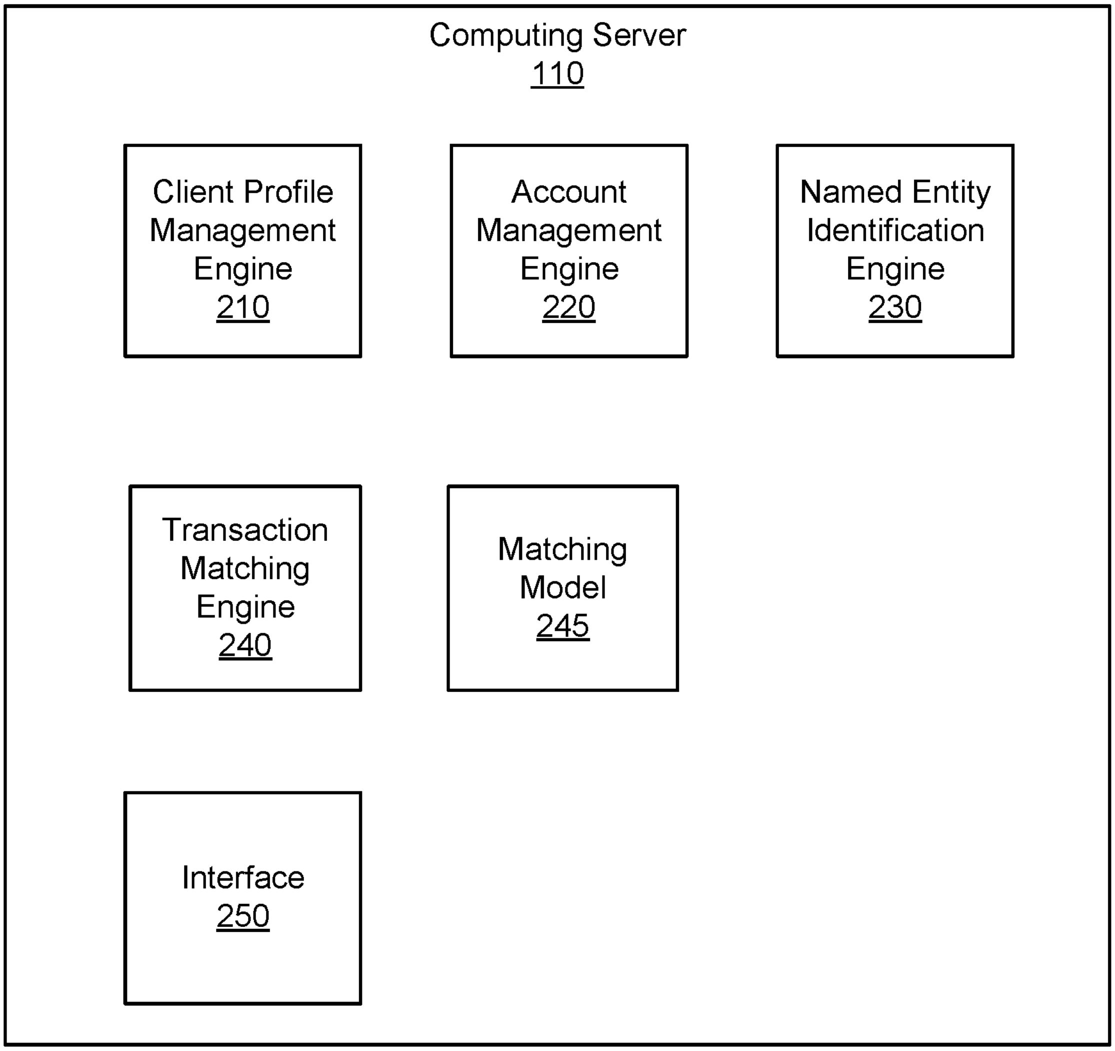
FIG. 2 is a block diagram illustrating components of an example computing server and an example secure server, in accordance with some embodiments.

FIG. 2 is a block diagram illustrating components of a computing server 110, in accordance with some embodiments. In some embodiments, the computing server 110 includes a client profile management engine 210, an account management engine 220, a named entity identification engine 230, a transaction matching engine 240, a matching model 245, an interface 250. In various embodiments, the computing server 110 may include fewer or additional components. The computing server 110 also may include different components. The functions of various components may be distributed in a different manner than described below. Moreover, while each of the components in FIG. 2 may be described in a singular form, the components may present in plurality. The components may take the form of a combination of software and hardware, such as software (e.g., program code comprised of instructions) that is stored on memory and executable by a processing system (e.g., one or more processors).

The client profile management engine 210 stores and manages end user data and transaction data of clients of the computing server 110. The computing server 110 can serve various clients associated with end users such as employees, vendors, and customers. For example, the client profile management engine 210 may store the employee hierarchy of a client to determine the administrative privilege of an employee in creating a transaction card account and in setting transaction and record verification rules. An administrator of the client may specify that certain employees from, for example, the financial department and managers have the administrative privilege to create cards for other employees. The client profile management engine 210 assigns metadata tags to transaction data of an organization to categorize the transactions in various ways, such as by transaction types, by merchants, by date, by amount, by card, by employee groups, etc. The client profile management engine 210 can monitor the spending of a client by category and also by the total spending. The spending amounts may affect the results of transaction and record verification rules that are specified by a client's system administrator. For example, a client may limit the total monthly spending of an employee group. The computing server 110 may deny further card payments after the total spending exceeds the monthly budget.

The transaction data stored by the client profile management engine 210 can include a record of a transaction, where the record includes data such as an amount of the transaction, the date of the transaction, a named entity that accepted a request by the end user to initiate the transaction (e.g., the merchant that accepted an end user's request to purchase the merchant's service), or combination thereof. The transaction data may be generated from various sources. For example, in some cases, the computing server 110 approves real-time transactions (e.g., credit card transactions) on behalf of an organization client. As such, an entry of the transaction is created as the computing server 110 approves the real-time transaction. In some cases, the computing server 110 may receive data in bulk from a third-party server 180 and the computing server 110 may parse the data to search for relevant transaction data. In yet other cases, the computing server 110 may receive transactions data from other platforms or software such as an accounting platform, a bank, etc.

The client profile management engine 210 may store the data in a suitable data structure. For example, for transaction data that are received from third-party server 180 (whether directly or via a filtering from the secure server 190), the client profile management engine 210 may store the record as provided by the secure server 190 or the third-party server 180. In some embodiments, the client profile management engine 210 may store emailed receipts as provided by the secure server 190 or the third-party server 180. In some embodiments, the data from the third-party server 180 may be unstructured such as data included in communications like emails. The client profile management engine 210 may parse the substance of the data and turn the data into structured transaction data.

The account management engine 220 creates and manages accounts including payment accounts such as transaction cards that are issued by the computing server 110. An account is associated with an end user such as an employee and corresponds to an end user transaction device 130 (e.g., end user transaction device 130 can be a physical card or a virtual credit card). A client may use the computing server 110 to issue domain-specific payment accounts such as company cards. The client enters account information such as the cardholder's name, role, and job title of the cardholder in the client's organization, limits of the card, and transaction rules associated with the card. In response to receiving the account information (e.g., from the client device 140), the account management engine 220 creates the card serial number, credentials, a unique card identifier, and other information needed for the generation of a payment account and corresponding card. The account management engine 220 associates the information with the cardholder's identifier. The computing server 110 communicates with a transaction card company (e.g., VISA, MASTERCARD) to associate the card account created with the identifier of the computing server 110 so that transactions related to the card will be stored at client profile management engine 210 with a mapping to identifiers for the account and the client's organization for querying transactions of the client organization. The account management engine 220 may also order the production of the physical card that is issued under the computing server 110.

A transaction rule may govern how a transaction may be handled during the approval process and/or after the transaction. For example, the cards and payment accounts created are associated with the transaction and documentation record verification rules that are specified by the client's administrator. An organization client may specify one or more selection criteria that certain transaction will need to be verified. Verification may be performed by matching the transaction with a documentation record such as a receipt. As discussed in further detail below, to reduce the burden on the employee or the administrator in verifying the transaction, the computing server 110 may automatically find a documentation record and match the record with the transaction, using various processes discussed below.

In some embodiments, the account management engine 220 creates rules for matching records to transactions. A client may specify rules under which records are to be matched to transactions by the computing server 110. The client may use the interface 144 of the client device 140 to specify the rules. The rules may include a location, time, named entity, end user, account, amount (e.g., purchase amount), or any suitable parameter related to a transaction. In one example of a rule, the client specifies that a documentation record is not required to be matched to a transaction for transaction amounts below 75 dollars for merchants in a travel category. In another example of a rule, the client specifies that a documentation record is required to be matched to a transaction for transactions made outside of the United States. The client may specify priority for rules such that a certain rule may override another rule. For example, the account management engine 220 may determine that, under the previous two examples of rules, the client has specified that rules for requiring record matching overrides rules for not requiring matching and cause the transaction matching engine 240 to match a documentation record to a transaction for, for example, a transaction made for a train ticket in Europe using an end user transaction device issued for an end user of the client.

Upon determining that matching is or is not needed using the rules created by the account management engine 220, the transaction matching engine 240 may annotate a record of the transaction with an indicator for the corresponding matching requirement (e.g., matching needed or not needed). This indicator may be used when generating a user interface for the client when managing matching statuses of past transactions Additionally, the indicator may be used to generate notifications to end users to notify the end users of the rules under which a documentation record is not necessary, which may prevent subsequent upload of records and save communication bandwidth and server storage resources. A client may establish such rules through an interface generated by the interface 250.

The named entity identification engine 230 identifies specific named entities (e.g., merchants) associated with various transactions. As described with respect to the client profile management engine 210, a transaction is associated with transaction data, which can include a record of a transaction. In a card purchase, for example, the transaction data may include merchant identifiers (MID), merchant category code (MCC), and the merchant name. The computing server 110 may use the named entities identified by the named entity identification engine 230 to impose entity-specific restrictions on a card. For example, an administrator of a client may specify that a specific card can only be used with a specific named entity and consequentially only approve transactions made with the specific named entity.

Typical computing servers might identify a named entity in a transaction record using a named entity recognition (NER) process that identifies named entities in transaction records based on string similarity metrics. For example, a transaction including the string "HEXA" might be identified as a named entity "Hexagon" because of the string similarity between the two strings. However, identifying named entities based on similarity metrics between transaction records can produce false positives and negatives. Transaction records often include noisy data, such as strings unrelated to the merchant name that a similarity-based NER approach may mistakenly identify as a merchant name. For example, in the transaction "TRIA*CIRC 14-21 348-882-82INK," a similarity-based NER approach may identify the last three letters, "INK," as the merchant rather than the actual merchant "CIRC." Transaction records may also include multiple abbreviations for the same merchant, such as "TRIA" and "TGL" for a merchant "Triangle," which a similarity-based NER approach may identify as different merchants. Transaction records may include random numbers and random strings that are not related to the actual real-world name of the merchant, or even misspellings of merchant names.

Rather than using a similarity based NER approach, the named entity identification engine 230 uses a transformer model to identify a named entity associated with a transaction record. The transformer model classifies a non-normalized version of the merchant name in the text string of the transaction record to a normalized merchant name in a list of candidate normalized merchant names. For example, for the transaction record, "TRIA *CIRC 14-21 348-882-821NK," the transformer model classifies the non-normalized version of the merchant name, "CIRC," as a normalized version of the merchant name "Circle." The transformer model may be an open-source large language model that is fine-tuned to perform the classification of the non-normalized merchant name. Alternatively, the transformer model may be an off-the-shelf large language model.

The named entity identification engine 230 trains the transformer model on pairs of transaction records. The transaction records in the pairs of transaction records may include historical transaction records collected and stored by the computing server 110 (e.g., at the data store 120). The transactions may have unique identifiers and may belong to a plurality of organization clients. In a pair of transaction records, each transaction record includes a text string including a non-normalized version of a merchant name. Each transaction record is labeled with a known normalized version of the merchant name. For example, the transaction record "TRIA*DIA 25-32 459-993-932NK" includes the non-normalized merchant name "DIA" and is labeled with the known normalized merchant name, "Diamond." The normalized merchant names may have the same unique identifiers as their corresponding historical transactions and may be stored at the data store 120. Each training pair is labelled by whether the transaction records in the pair correspond to the same merchant. A pair of transactions corresponding to the same named entity may have a label of "1," while a pair of transaction records corresponding to different named entities may have a label of "0." For example, if the transaction record "TRIA*DIA 25-32 459-993-932NK" which has a normalized named entity name "Diamond" is paired with the transaction record "DIAMOND SUBCRIPTION*2134-#21305" which also has the normalized named entity name "Diamond," the pair would be labelled with "1." The pairs of transactions may be manually labelled by an agent or automatically labelled based on a match between their normalized merchant names.

In an inference process, the named entity identification engine 230 inputs a text string of a transaction record and a set of similar transactions into the trained transformer model. The set of similar transactions include historical transactions stored by the computing server 110 (e.g., at the data store 120). The similar transactions may belong to the same organization client as the transaction record or may belong to different organization clients. Each similar transaction may be associated with a normalized merchant name that has the same unique identifier as the transaction. The normalized merchant names may be generated manually or by the trained transformer model. The named entity identification engine 230 may input the text string of the transaction record and similar transactions in natural language, for example by providing the transformer model with a prompt. The named entity identification engine 230 may additionally generate a list of candidate named entities and provide the list to the transformer model. The list of candidate named entities may include normalized merchant names associated with the historical transactions collected and stored by the client device 140. In one example, the list of candidate named entities includes normalized merchant names associated with the transactions in the set of similar transactions. In another example, the list of candidate named entities may include normalized merchant names with high semantic similarity to the text of the transaction record, such as "Triangle" and "Circle" for "TRIA*CIRC 14-21 348-882-821NK." In some embodiments, the named entity identification engine 230 may provide the transformer model with additional information about the transaction record, for example information received from the transaction terminal 150. At a high level, during the inference process, the trained transformer model identifies which of the similar transactions has the same named entity as the transaction record, identifies the normalized named entity name associated with the identified similar transaction (e.g., using the unique identifier), and checks that the identified normalized named entity name is on the list of candidate named entities. The named entity identification engine 230 receives, as output from the transformer model, a normalized named entity that the non-normalized named entity of the transaction record can be classified to.

In some embodiments, the named entity identification engine 230 may receive an output from the transformer model indicating that the non-normalized named entity cannot be classified as a normalized named entity. For example, a merchant may be a restaurant that the computing server 110 does not recognize or merchant with which the end user transaction device 130 has not previously performed a transaction. The named entity identification engine 230 may identify the non-normalized merchant name as belonging to a new merchant and may generate a normalized version of the non-normalized version of the merchant name (e.g., by using the non-normalized version as the normalized version or by performing an internet search for the merchant name). The named entity identification engine 230 may store the normalized version of the merchant name at the data store 120. The named entity identification engine 230 may create a new merchant profile for the merchant.

In some embodiments, the transformer model may be an off-the-shelf large language model. The named entity identification engine 230 may generate a prompt for the transformer model. The prompt may include a request that the transformer model classify the non-normalized merchant name of a transaction record as a normalized merchant name. The prompt may include the transaction record, a set of similar transactions and their associated merchants, or a candidate named entity list. For example, the named entity identification engine 230 may generate a prompt like "Identify the name of the merchant for [transaction record] based on the similarity of [transaction record] and [set of similar transactions, set of normalized named entity]. The merchant may be one of the following merchants: [candidate named entity list].” The named entity identification engine 230 may provide the prompt to the transformer model for execution.

The named entity identification engine 230 generates the set of similar transaction records to input into the transformer model using embeddings. The named entity identification engine 230 generates an embedding of the transaction record and compares the generated embedding to embeddings for historical transactions. The named entity identification engine 230 generates an embedding of the transaction record by passing the transaction record through an embedding model. The embedding model turns the text of the transaction record into an embedding (e.g., a vector) in a latent space. The embedding encodes the text of the transaction record such that similar transaction records with embeddings in the same latent space will have similar embeddings. The embedding model may be a transformer model and may be an off the shelf model such as TF-IDF or BM25. The named entity identification engine 230 may compute the embeddings of the historical transactions using the same embedding model, such that the embeddings of the historical transactions and the embeddings of the transaction record are in the same latent space. The named entity identification engine 230 may store mappings between embeddings and the historical transactions to which they correspond. The named entity identification engine 230 compares the embedding of the transaction record to embeddings of historical transactions. In some embodiments, the named entity identification engine 230 compares the embedding of the transaction record to embeddings of historical transactions by computing a distance between the embedding of the transaction record and the embeddings of the historical transactions, for example computing the Euclidean distance, the cosine similarity, or the dot product. In other embodiments, the named entity identification engine 230 compares the embedding of the transaction record to embeddings of historical transactions by clustering the embeddings of the historical transactions and identifying a cluster to which the embedding of the transaction record belongs. The named entity identification engine 230 generates the set of similar transactions based on the historical transactions with embeddings closest to the embedding of the transaction record (e.g., the top 100 most similar transactions, transactions within a threshold similarity of embeddings).

In some embodiments, the named entity identification engine 230 identifies specific named entities associated with bank transfer payment records. Much like how the named entity identification engine may use a transformer model to identify the named entity associated with a transaction record, the named entity identification engine 230 may use a transformer model to identify the named entity associated with a bank transfer payment record. However, instead of training the transformer model on pairs of transaction records, the named entity identification engine 230 trains the transformer model on pairs of bank transfer payment records. A pair of bank transfer payment records corresponding to the same named entity may have a label of “1,” while a pair of bank transfer payment records corresponding to different named entities may have a label of “0.”

U.S. patent application Ser. No. 17/351,120, entitled “Real-time Named Entity Based Transaction Approval” and filed on Jun. 17, 2021, is incorporated in its entirety herein for all purposes.

The transaction matching engine 240 matches a documentation record that may be generated by a third-party named entity 170 with a transaction stored in the computing server 110, such as a transaction made using an end user transaction device 130. The transaction matching engine 240 receives data from the secure server 190 or from the third-party server 180. The data may include one or more documentation records that are mixed with other information such as irrelevant communication. The data may be transmitted to the computing server 110 in bulk such as in a communication payload that includes a collection of communications, which can be a collection of emails, collections of receipts that may or may not be relevant, or in other forms. The transaction matching engine 240 may in turn identify the relevant documentation record, parse the relevant information, and match the documentation record with a transaction stored in the computing server 110. For example, where the documentation record is a receipt inside of a communication payload that includes a number of emails associated with an employee, the computing server 110 may search for data associated with the record, such as the timestamp of the email or the sender of the email, even though this data may not be directly located in the documentation record itself. The transaction matching engine 240 may receive the documentation record unprompted (e.g., documentation record may be transmitted from third-party server 180 through push mechanisms such as webhook) or as a result of a request made to the secure server 190 or the third-party server 180. Requests may be initiated by the computing server 110, manually by an administrator or automatically. Requests may be initiated periodically, or may be initiated in response to other stimuli, for example when the computing server receives a transaction that fits the matching criteria selected by the organization client.

The transaction matching engine 240 may process the documentation record. Processing the documentation record may include extracting attributes from the documentation record, wherein an attribute includes data or metadata associated with the documentation record. For example, when the documentation record documents a transaction between an end user and a merchant, attributes may include the date of the transaction, the amount transacted, the name of the merchant, or personal data about the end user, such as the end user's credit card information. When the documentation record is included an email, attributes may be included in various header fields (e.g., the “To” field, the “From” field, the “Subject” field), the body, hidden text, attachments, timing data, or any other data commonly found in emails.

The transaction matching engine 240 may perform different methods of attribute extraction depending on the medium in which the documentation record is provided or depending on the server it receives the documentation record from. For example, a documentation record received from the third-party server 180 may contain known attributes, such as the identity of the named entity, which may allow the transaction matching engine 240 to extract fewer attributes overall from the record. The transaction matching engine 240 may extract attributes using a text search method or natural language processing.

The transaction matching engine 240 may match a documentation record to a past transaction. The transaction matching engine 240 may identify a set of candidate past transactions to match the documentation record to. A set of candidate past transactions may include transactions with timestamps within a time window corresponding to a timing record included in the documentation record. For example, if a documentation record contains timing data that suggests it was created on October $5^{th}$ at 10:32 am EST, candidate transactions may be transactions with timestamps on October $5^{th}$, or, more granularly, timestamps on October $5^{th}$ from 9:32 am EST to 11:32 am EST, for example. The transaction matching engine 240 may determine a match between a documentation record and a candidate past transaction by matching attributes extracted from the documentation record to transaction metadata. For example, where the documentation record is an electronic receipt, the transaction matching engine 240 may identify candidate transactions by identifying a message header in the electronic receipt, determining, using the message header, that the electronic receipt was transmitted from an automated system associated with a particular third-party named entity to an electronic address of an end user, and identifying a set of candidate transactions incurred between a plurality of third-party named entities and the transaction account associated with the electronic address.

In various embodiments, matching may be performed using various algorithms, rules, and other criteria. For example, certain fields may require a closer match (or even an exact match) while other fields may be matched more loosely. In some embodiments, matching may also be performed using scoring of the matching information in various fields. For example, a match between a documentation record and a transaction may be determined by a match between the record's and the transaction's respective amounts, named entities (e.g., merchants), dates, or any suitable data related to a transaction that is recorded or reported in the execution of a transaction (e.g., by the transaction terminal 150). The transaction matching engine 240 may assign weights to the attributes that match the metadata of one of the unverified transactions and sum the weighted attributes to generate a score. The transaction matching engine 240 may compare the generated score to a threshold score and determine a match if the generated score exceeds the threshold score. A client may specify the threshold score value to the computing server 110 (e.g., via the interface 144). The transaction matching engine 240 may stipulate that one of the attributes be an exact match in order for the record to match the transaction. The transaction matching engine 240 may alternatively or additionally stipulate that if some attributes do not match, the record is not a match with the transaction.

The transaction matching engine 240 may apply the matching model 245 to a documentation record and one or more past transactions to determine if the record matches a past transaction. The matching model 245 receives, as input, a processed or unprocessed documentation record or representation thereof (e.g., a feature vector where values of the vector are related to the documentation record) and one or more past transactions. The matching model 245 determines, as output, a match between a documentation record and a past transaction. The matching model 245 may output a level of confidence associated with the match. The matching model 245 may include a ruled based algorithm, such as a heuristic algorithm, a decision tree, or a machine learning model.

The matching model 245 may include one or more machine learning models that are trained to recognize text and natural language. One or more machine learning models may also be trained to identify relevant fields in a documentation record or past transaction, such as the date, the merchant name, and the transaction amount. One or more machine learning models may also be trained to recognize named entities.

The interface 250 includes interfaces that are used to communicate with different parties and servers. For example, the interface 250 may display that a documentation record is automatically found by the computing server 110 for a particular transaction and mark the transaction as verified. The interface 250 may take the form of a SaaS platform that provides clients with access of various functionalities provided by the computing server 110. The interface 250 provides a portal in the form of a graphical user interface (GUI) for clients to create payment accounts, manage transactions, specify rules of each card, and verify records of transactions incurred using the cards. The interface 250 is in communication with the application 142 and provides data to render the application 142.

In some embodiments, the interface 250 also includes an API for clients of the computing server 110 to communicate with the computing server 110 through machines. The API allows the clients to retrieve the computing server 110 stored in the data store 120, send query requests, and make settings through a programming language. Various settings, creation of cards, rules on the cards, rules of verifying records, and other functionalities of the various engines 210, 220, 230, and 240 or model 245 may be changed by the clients through sending commands to the API.

Named Entity Identification Process

Figure 3:
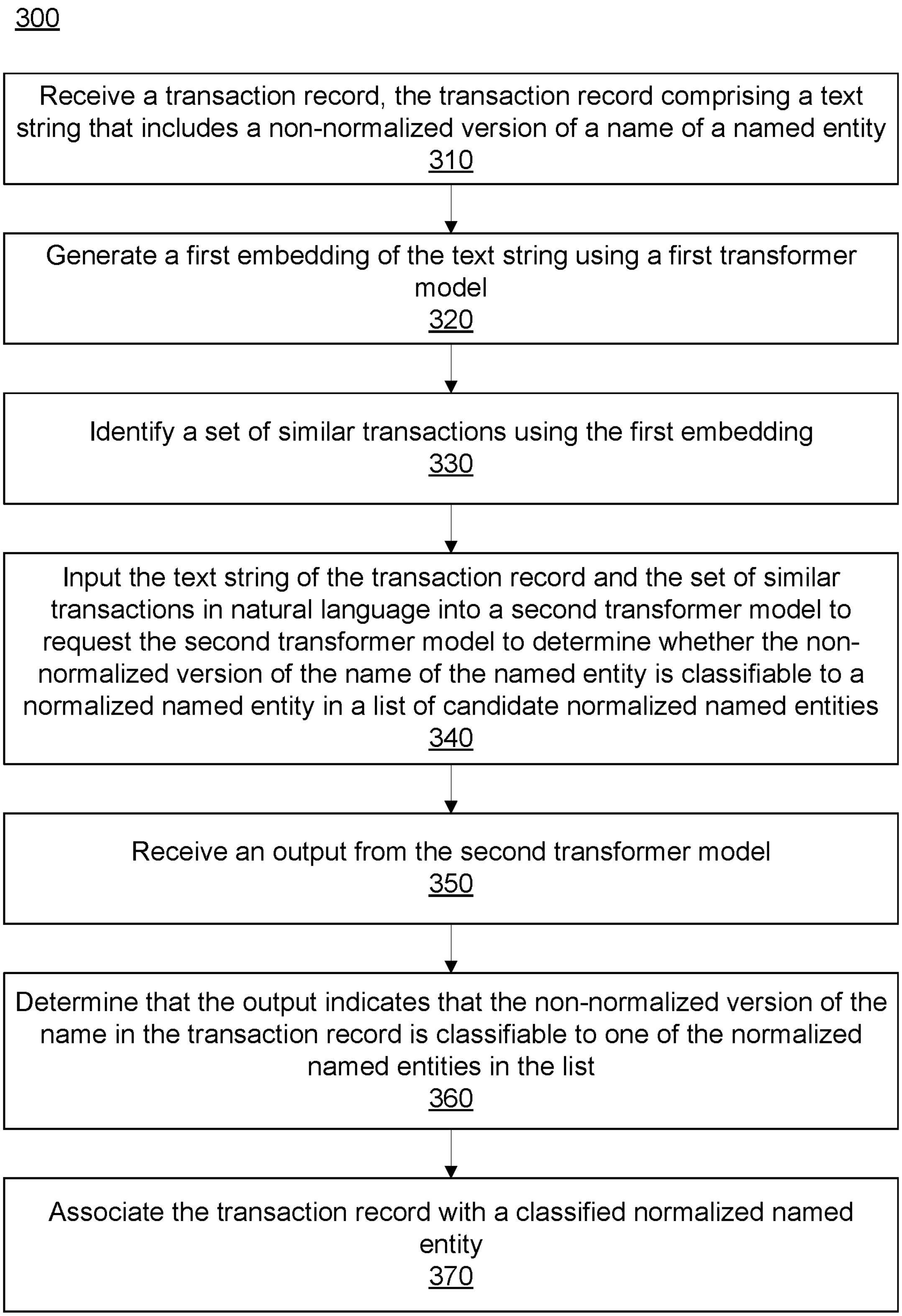
FIG. 3 is a flowchart for a method of identifying a named entity associated with a transaction record, in accordance with some embodiments.

FIG. 3 is a flowchart for a method of identifying a named entity associated with a transaction record. While the steps in process 300 are illustrated graphically in FIG. 3 as sequences of steps, some of the steps may occur in different sequences than illustrated or may occur concurrently with other steps. Also, while the process 300 is depicted as a single series, in various embodiments and situations a process may be further broken down into multiple series.

The process 300 begins with the computing server 110 receiving 310 a transaction record. A transaction record includes data about a transaction, for example an amount of the transaction, a date of the transaction, a named entity that accepted a request by an end user to initiate the transaction, or a combination thereof. A transaction record includes a text string that includes a non-normalized version of a name of a named entity, for example the name of a merchant or the name of an account associated with the transaction. Examples of transaction records are real-time approval payloads produced as a result of credit card transactions with POS systems and statements indicating bank transfers between accounts. A named entity (e.g., the third-party named entity 170) may be a party associated with the transaction. For example, the named entity may be a merchant that provides goods or services for purchase by a user using the end user transaction device 130, such as in the situation where an employee uses a virtual credit card issued by the computing server 110 on behalf of the employer to make a purchase with a merchant. Another example of a named entity is a bank which conducts transactions with a company that is the client of the computing server 110. The transaction record may be generated by a server of the named entity (e.g., the third-party server 180 of the third-party named entity 170) or by the transaction terminal 150. For example, after a purchase using a POS terminal, the terminal or server may automatically generate a transaction record in the form of a paper or an electronic receipt. The computing server 110 may receive the transaction record from the transaction terminal 150, from the third-party server 180, or from upload by a user (e.g., a screenshot of a credit card transaction, an image of a paper receipt).

The computing server 110 generates 320 a first embedding of the text string using a first transformer model. The first transformer model may be an embedding model. The embedding model encodes the text of the transaction record as a vector in a latent space, or "an embedding." The embedding is a low-dimensional representation of the text of the transaction record. The latent space is made up by the set of embeddings output by the embedding model and is of lower dimensionality than the features of the text of the transaction record. The latent space is also organized such that the similarity between transaction records is represented by the distance between their embeddings. The closer the embeddings are (e.g., smaller distance between vectors in the latent space), the more similar the transaction records are. The architecture of the embedding model may be a neural network including a plurality of layers (e.g., fully connected layers, activation layers, etc.). The embedding model may be an off the shelf embedding model such as TF-IDF, BM25, or string edit distance.

The computing server 110 identifies 330 a set of similar transactions using the first embedding by comparing the first embedding representing the transaction record to second embeddings representing historical transactions. The computing server 110 collects historical transactions belonging to a plurality of organization clients and stores them at the data store 120. Each historical transaction may be associated with a normalized named entity name that is stored along with the historical transaction at the data store 120. The normalized named entity names may be generated manually or by a transformer model (e.g., the second transformer model, described with respect to step 340). The second embeddings are generated by applying the first transformer model to the historical transactions. As such, the first embedding and the second embeddings are in the same latent space. The computing server 110 compares the first embedding to each of the second embeddings. In some embodiments, the computing server 110 compares the first embedding the second embeddings by computing a distance between the first embedding and each of the second embeddings, for example computing the Euclidean distance, the cosine similarity, or the dot product. In other embodiments, the computing server 110 compares the first embedding to the second embeddings by clustering the second embeddings (e.g., using k-means clustering) and identifying a cluster to which the first embedding belongs. The computing server 110 generates the set of similar transactions based on the historical transactions with second embeddings closest to the first embedding (e.g., the top 100 most similar transactions, transactions within a threshold similarity of embeddings).

The computing server 110 inputs 340 the text string of the transaction record and the set of similar transactions in natural language into a second transformer model to request the second transformer model to determine whether the non-normalized version of the name of the named entity is classifiable to a normalized named entity in a list of candidate normalized named entities. In some embodiments, the second transformer model is an open-source large language model that is fine-tuned to perform the classification of the non-normalized merchant name. In these embodiments, the computing server 110 may pass the model the text of the transaction record and the set of similar transactions without providing a prompt to the second transformer model. The computing server 110 may also provide the model with the normalized named entity names associated with the similar transactions. In other embodiments, the transformer model is an off-the-shelf large language model. In these embodiments, the computing server 110 may generate a prompt for the transformer model. The prompt may include a request that the transformer model classify the non-normalized merchant name of the transaction record as a normalized merchant name. The prompt may include the transaction record and the set of similar transactions and their associated normalized named entity names. For example, the computing server 110 may generate a prompt like "Identify the name of the merchant for [transaction record] based on the similarity of [transaction record] to [set of similar transactions, set of normalized named entity names]." The computing server 110 may provide the prompt to the transformer model for execution. The computing server 110 may additionally generate a list of candidate named entities and provide the list to the transformer model. The list of candidate named entities may include normalized named entity names associated with the historical transactions collected and stored by the client device 140. In one example, the list of candidate named entities includes normalized named entity names associated with the transactions in the set of similar transactions. In another example, the list of candidate named entities may include normalized named entity names with high semantic similarity to the text of the transaction record.

The computing server 110 receives 350 an output from the second transformer model, which may either indicate that the non-normalized named entity name in the transaction record is classifiable to a normalized named entity in the list of candidate normalized named entities or that the non-normalized named entity cannot be classified as a normalized named entity in the list. The computing server 110 determines 360 that the output indicates that the non-normalized version of the name in the transaction record is classifiable to one of the normalized named entities in the list.

The computing server 110 associates 370 the transaction record with the normalized named entity to which the non-normalized named entity is classifiable. For example, the computing server 110 may store the transaction record and the normalized named entity in the data store 120. The computing server 110 may assign both the transaction record and the normalized named entity with the same unique identifier.

Figure 4:
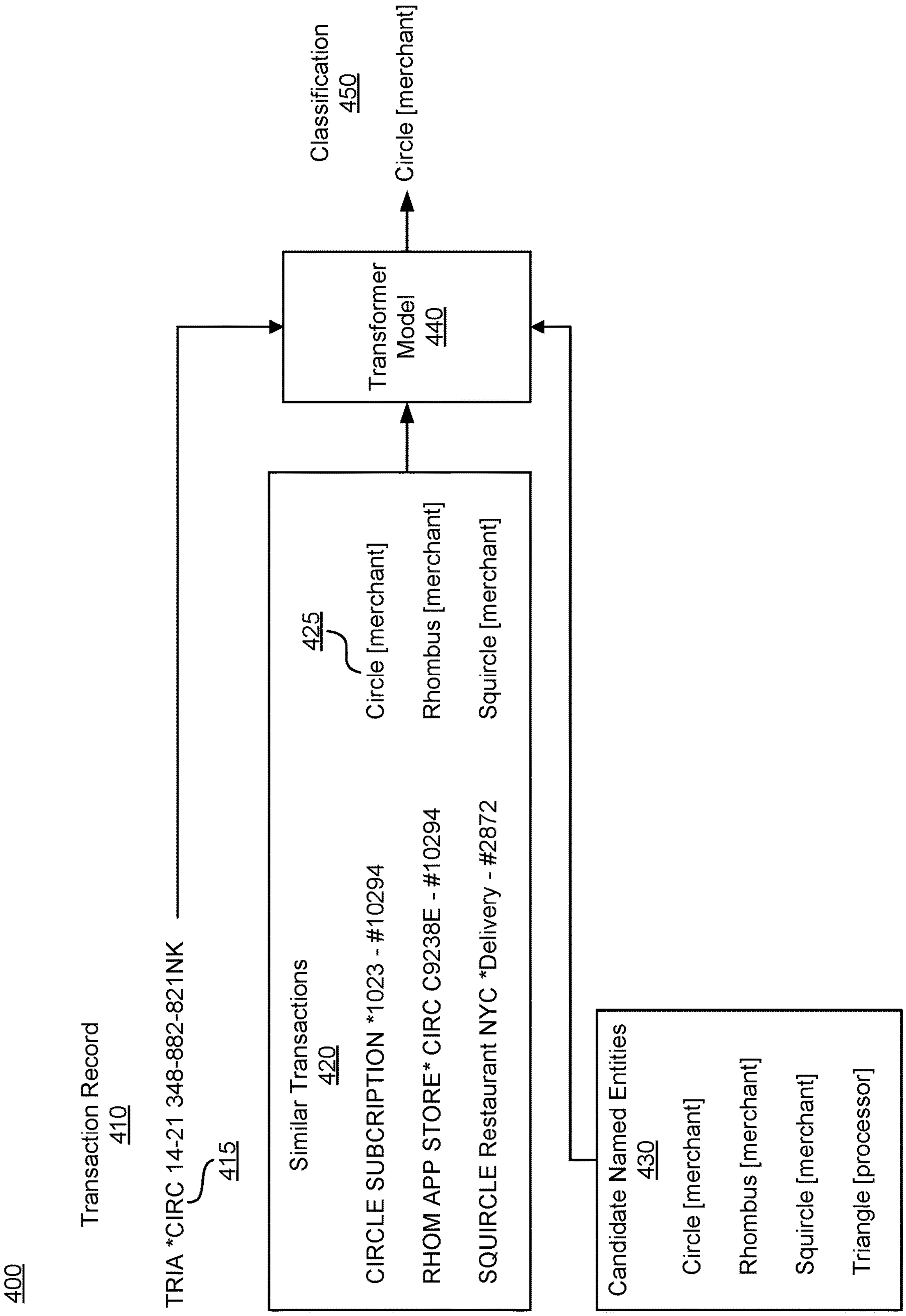
FIG. 4 is a block diagram illustrating an example named entity identification process, in accordance with some embodiments.

FIG. 4 is a block diagram illustrating an example named entity identification process. The block diagram 400 illustrates a named entity identification process for a transaction record 410. The transaction record 410 includes the text string "TRIA*CIRC 14-21 348-882-821NK" which includes a non-normalized named entity 415, "CIRC. The named entity identification engine 230 generates a set of similar transactions 420 that are similar to the transaction record 410, "CIRCLE SUBCRIPTION*1023-#10294," "RHOMBUS APP STORE*CIRC C9238E-#10294," and "SQUIRCLE Restaurant NYC*Delivery-#2872." Each of the similar transactions is labeled with a corresponding normalized named entity 425. For example, the similar transaction "CIRCLE SUBCRIPTION*1023-#10294," is labeled with the normalized named entity "Circle," and the similar transaction "RHOM APP STORE*CIRC C9238E-#10294" is labeled with the normalized named entity "Rhombus." The named entity identification engine 230 also generates a list of candidate named entities 430. In the example of FIG. 4, the candidate named entity list 430 includes the normalized named entities associated with the similar transactions 420, "Circle," "Rhombus," and "Squircle" as well as a normalized named entity with a high semantic similarity to the text of the transaction record 410, "Triangle." The transformer model 440 receives the transaction record 410, the set of similar transactions 420, and the set of candidate named entities 430 as inputs. The transformer model 440 outputs a classification 450. In the depicted example, the transformer model 440 classifies the transaction record 410 as belonging to the normalized named entity "Circle."

Machine Learning Models

The computing server 110 may use machine learning models to identify relevant documentation records in communication payloads. The computing server 110 may accumulate a large number of past communication payloads, wherein some communication payloads contain documentation records, and some do not. The computing server 110 may use the past communication payloads as a set of training samples to iteratively train one or more machine learning models that can be used to identify documentation records in communication payloads.

The computing server 110 may use machine learning models to match documentation records with transactions. One or more machine learning models may be part of the matching model 245. The computing server 110 may accumulate a large number of past documentation records and corresponding transaction records as well as documentation records and transaction records that do not have corresponding matches. The computing server 110 may use the past documentation records and transaction records as a set of training samples to iteratively train one or more machine learning models that can be used to match documentation record with transactions.

A training sample may include a label for supervised training. The label may be generated by a manual process or by an automatic process. For example, in training a model that is used to identify a documentation record in a communication payload, the training samples may include past communication records with the presence of a documentation record as labels.

In some embodiments, a machine learning model may also be used to identify the useful fields in a communication payload or a documentation record. In such cases, the labels of training samples may be locations of the fields. In some embodiments, certain common communication payloads or documentation records may have rule-based models to help identifying information. For example, for common large merchants such as chain restaurants, online retailing platforms, large payment POS services, the documentation records of those merchants may follow a standard format. A rule-based model may be used to locate the standard fields in those records. In some cases, part of the training samples includes labels while other training samples do not include labels but are grouped with labeled samples through a process such as clustering and word embeddings.

In various embodiments, a wide variety of machine learning techniques may be used. Examples of which include different forms of unsupervised learning, clustering, embeddings such as word embeddings, support vector regression (SVR) model, random forest classifiers, support vector machines (SVMs) such as kernel SVMs, gradient boosting, linear regression, logistic regression, and other forms of regressions. Deep learning techniques such as neural networks, including convolutional neural networks (CNN), recurrent neural networks (RNN), and long short-term memory networks (LSTM), may also be used. Each transaction dataset may be converted to a feature vector that includes different dimensions. By way of example, strings in the transaction data may be converted to word embeddings using known techniques Word2Vec or another technique. The word embeddings can be one or more dimensions of the feature vector. Other data fields may be turned into various dimensions of a feature vector representing a transaction data. The feature vectors can be inputted into the machine learning model to iteratively train the machine learning model. A series of transactions may also be converted to a time series.

In various embodiments, the training techniques for iteratively training a machine learning model may be supervised, semi-supervised, or unsupervised. In supervised training, the machine learning algorithms may be trained with a set of training samples that are labeled. For example, a past communication payload can be associated with a label. The labels for each training sample may be binary or multi-class. In some cases, an unsupervised learning technique may be used. The samples used in training are not labeled. Various unsupervised learning techniques such as clustering may be used. In some cases, the training may be semi-supervised with the training set having a mix of labeled samples and unlabeled samples.

A machine learning model is associated with an objective function, which generates a metric value that describes the objective goal of the training process. For example, the training intends to reduce the error rate of the model in generating predictions of the results (whether the result is the presence of a documentation record within a communication payload or a match between a documentation record and a transaction). In such a case, the objective function may monitor the error rate of the machine learning model. In transaction series analysis, the objective function of the machine learning algorithm may be the value different in predicting the recurring frequency in a training set. Such an objective function may be called a loss function. Other forms of objective functions may also be used, particularly for unsupervised learning models whose error rates are not easily determined due to the lack of labels. In various embodiments, the error rate may be measured as cross-entropy loss, L1 loss (e.g., the absolute distance between the predicted value and the actual value), L2 loss (e.g., root mean square distance).

A machine learning model includes certain layers, nodes, kernels, and/or coefficients. Training of a machine learning model includes iterations of forward propagation and backpropagation. Each layer in a neural network may include one or more nodes, which may be fully or partially connected to other nodes in adjacent layers. In forward propagation, the neural network performs the computation in the forward direction based on outputs of a preceding layer. The operation of a node may be defined by one or more functions. The functions that define the operation of a node may include various computation operations such as convolution of data with one or more kernels, pooling, recurrent loop in RNN, various gates in LSTM, etc. The functions may also include an activation function that adjusts the weight of the output of the node. Nodes in different layers may be associated with different functions.

Each of the functions in the neural network may be associated with different coefficients (e.g., weights and kernel coefficients) that are adjustable during training. In addition, some of the nodes in a neural network may each also be associated with an activation function that decides the weight of the output of the node in forward propagation. Common activation functions may include step functions, linear functions, sigmoid functions, hyperbolic tangent functions (tanh), and rectified linear unit functions (ReLU). After input is provided into the neural network and passes through a neural network in the forward direction, the results may be compared to the training labels or other values in the training set to determine the neural network's performance. The process of prediction may be repeated for other transactions in the training sets to compute the value of the objective function in a particular training round. In turn, the neural network performs backpropagation by using gradient descent such as stochastic gradient descent (SGD) to adjust the coefficients in various functions to improve the value of the objective function.

Multiple iterations of forward propagation and back-propagation may be performed. Training may be completed when the objective function has become sufficiently stable (e.g., the machine learning model has converged) or after a predetermined number of rounds for a particular set of training samples. Different machine learning models may be trained for different purposes.

Additional Considerations

The general architecture disclosed herein has applications in various areas, such as a payment transaction verification process. For example, in a credit card transaction, the credit card company logs data for the transaction incurred between an end user and a merchant, and the merchant provides a record of the transaction to the end user. This record can be a receipt such as an emailed receipt or a printed receipt. In some embodiments, a computing server verifies the transactions by matching transaction data (e.g., amount of the transaction, date of the transaction, and name of the merchant) provided by the credit card company against the transaction data parsed from a receipt. Instead of prompting the end user to provide the receipt for verification, the computing server can operate on standby until, unprompted, the end user provides the receipt. Thus, the computing server does not expend unnecessary processing and network bandwidth resources to acquire records from end users for verifying transactions.

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Embodiments according to the invention are in particular disclosed in the attached claims directed to a method and a computer program product, wherein any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter which can be claimed comprises not only the combinations of features as set out in the disclosed embodiments but also any other combination of features from different embodiments. Various features mentioned in the different embodiments can be combined with explicit mentioning of such combination or arrangement in an example embodiment. Furthermore, any of the embodiments and features described or depicted herein can be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In some embodiments, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

What is claimed is:

1. A computer-implemented method, comprising:

receiving a transaction record, the transaction record comprising a text string that includes a non-normalized version of a name of a named entity;

generating a first embedding of the text string using a first transformer model, the first embedding being in a latent space of the first transformer model;

identifying a set of similar transactions using the first embedding, wherein identifying the set of similar transactions comprises comparing the first embedding to second embeddings representing historical transactions, the first embedding and the second embeddings in the latent space of the first transformer model;

inputting the text string of the transaction record and the set of similar transactions in natural language into a second transformer model to request the second transformer model to determine whether the non-normalized version of the name of the named entity is classifiable to a normalized named entity in a list of candidate normalized named entities, wherein the second transformer model is a large language model that is fine-tuned to perform classification of the non-normalized version of the name of the named entity and is trained on training examples, each training example comprising a pair of transaction records comprising a text string that includes a non-normalized version of a name of a named entity, each training example labelled by whether the pair of transaction records are classifiable to a same normalized named entity in the list;

receiving an output from the second transformer model;

determining that the output indicates that the non-normalized version of the name in the transaction record is classifiable to one of the normalized named entities in the list; and associating the transaction record with a classified normalized named entity.

2. The method of claim 1, further comprising:

determining that the output indicates that the non-normalized version of the name in the transaction record is not classifiable to one of the normalized named entities in the list;

generating a normalized version of the name in the transaction record; and storing the generated normalized version of the name.

3. The method of claim 1, wherein the first transformer model is an off-the-shelf embedding model.

4. The method of claim 1, wherein the list of candidate normalized named entities comprises normalized named entities with high semantic similarity to the text string of the transaction record.

5. The method of claim 1, wherein the list of candidate normalized named entities comprises normalized named entities associated with the transactions in the set of similar transactions.

6. The method of claim 1, wherein inputting the text string of the transaction record and the set of similar transactions in natural language into the second transformer model further comprises inputting additional information about the transaction record into the second transformer model.

7. The method of claim 1, wherein the transaction record is a bank transfer payment record and the set of similar transactions is a set of similar bank transfer payment records.

8. A non-transitory computer-readable storage medium configured to store computer code comprising instructions, wherein the instructions, when executed by one or more processors, cause the one or more processors to:

receive a transaction record, the transaction record comprising a text string that includes a non-normalized version of a name of a named entity;

generate a first embedding of the text string using a first transformer model, the first embedding being in a latent space of the first transformer model;

identify a set of similar transactions using the first embedding, wherein identifying the set of similar transactions comprises comparing the first embedding to second embeddings representing historical transactions, the first embedding and the second embeddings in the latent space of the first transformer model;

input the text string of the transaction record and the set of similar transactions in natural language into a second transformer model to request the second transformer model to determine whether the non-normalized version of the name of the named entity is classifiable to a normalized named entity in a list of candidate normalized named entities, wherein the second transformer model is a large language model that is fine-tuned to perform classification of the non-normalized version of the name of the named entity and is trained on training examples, each training example comprising a pair of transaction records comprising a text string that includes a non-normalized version of a name of a named entity, each training example labelled by whether the pair of transaction records are classifiable to a same normalized named entity in the list;

receive an output from the second transformer model;

determine that the output indicates that the non-normalized version of the name in the transaction record is classifiable to one of the normalized named entities in the list; and associate the transaction record with a classified normalized named entity.

9. The non-transitory computer-readable storage medium of claim 8, further comprising instructions that, when executed by the one or more processors, cause the one or more processors to:

determine that the output indicates that the non-normalized version of the name in the transaction record is not classifiable to one of the normalized named entities in the list;

generate a normalized version of the name in the transaction record; and store the generated normalized version of the name.

10. The non-transitory computer-readable storage medium of claim 8, wherein the first transformer model is an off-the-shelf embedding model.

11. The non-transitory computer-readable storage medium of claim 8, wherein the list of candidate normalized named entities comprises normalized named entities with high semantic similarity to the text string of the transaction record.

12. The non-transitory computer-readable storage medium of claim 8, wherein the list of candidate normalized named entities comprises normalized named entities associated with the transactions in the set of similar transactions.

13. The non-transitory computer-readable storage medium of claim 8, wherein the instruction for inputting the text string of the transaction record and the set of similar transactions in natural language into the second transformer model further comprises instructions that, when executed by the one or more processors, cause the one or more processors to input additional information about the transaction record into the second transformer model.

14. The non-transitory computer-readable storage medium of claim 8, wherein the transaction record is a bank transfer payment record and the set of similar transactions is a set of similar bank transfer payment records.

15. A system, comprising:

one or more processors and memory, the memory configured to store instructions, wherein the instructions, when executed by the one or more processors, cause the one or more processors to:

receive a transaction record, the transaction record comprising a text string that includes a non-normalized version of a name of a named entity;

generate a first embedding of the text string using a first transformer model, the first embedding being in a latent space of the first transformer model;

identify a set of similar transactions using the first embedding, wherein identifying the set of similar transactions comprises comparing the first embedding to second embeddings representing historical transactions, the first embedding and the second embeddings in the latent space of the first transformer model;

input the text string of the transaction record and the set of similar transactions in natural language into a second transformer model to request the second transformer model to determine whether the non-normalized version of the name of the named entity is classifiable to a normalized named entity in a list of candidate normalized named entities, wherein the second transformer model is a large language model that is fine-tuned to perform classification of the non-normalized version of the name of the named entity and is trained on training examples, each training example comprising a pair of transaction records comprising a text string that includes a non-normalized version of a name of a named entity, each training example labelled by whether the pair of transaction records are classifiable to a same normalized named entity in the list;

receive an output from the second transformer model;

determine that the output indicates that the non-normalized version of the name in the transaction record is classifiable to one of the normalized named entities in the list; and associate the transaction record with a classified normalized named entity.

16. The system of claim 15, further comprising instructions that, when executed by the one or more processors, cause the one or more processors to:

determine that the output indicates that the non-normalized version of the name in the transaction record is not classifiable to one of the normalized named entities in the list;

generate a normalized version of the name in the transaction record; and store the generated normalized version of the name.

17. The system of claim 15, wherein the first transformer model is an off-the-shelf embedding model.

18. The system of claim 15, wherein the list of candidate normalized named entities comprises normalized named entities with high semantic similarity to the text string of the transaction record.

19. The system of claim 15, wherein the list of candidate normalized named entities comprises normalized named entities associated with the transactions in the set of similar transactions.

20. The system of claim 15, wherein the instruction for inputting the text string of the transaction record and the set of similar transactions in natural language into the second transformer model further comprises instructions that, when executed by the one or more processors, cause the one or more processors to input additional information about the transaction record into the second transformer model.

* * * * *